United States Patent [19]
Gerard et al.

[11] Patent Number: 5,948,527
[45] Date of Patent: Sep. 7, 1999

[54] ADHESIVE COMPOSITIONS COMPRISING BLOCK COPOLYMERS OF A MONOVINYLAROMATIC COMPOUND AND BUTADIENE

[75] Inventors: Eric-Jack Gerard, Amsterdam, Netherlands; Noel Raymond Maurice De Keyzer, Louvain-La-Neuve, Belgium; Birgitte Maria Ludovica Christine Van De Vliet, Amsterdam, Netherlands

[73] Assignee: Shell Oil Company, Houston, Tex.

[21] Appl. No.: 09/009,062

[22] Filed: Jan. 20, 1998

Related U.S. Application Data

[62] Division of application No. 08/812,226, Mar. 6, 1997, Pat. No. 5,750,607.

[30] Foreign Application Priority Data

Aug. 3, 1996 [EP] European Pat. Off. .............. 96301608

[51] Int. Cl.$^6$ ............................. A61F 13/15; A61L 15/16; B32B 7/14
[52] U.S. Cl. .................................... 428/355 BL; 428/500; 428/40.1; 442/59; 604/372; 604/358
[58] Field of Search ........................... 428/355 BL, 500, 428/40.1; 442/59; 604/372, 358

[56] References Cited

U.S. PATENT DOCUMENTS

| | | | |
|---|---|---|---|
| H1622 | 12/1996 | Himes | 525/89 |
| 3,658,740 | 4/1972 | Marrs et al. | 525/89 |
| 4,101,482 | 7/1978 | Doss et al. | 524/271 |
| 4,136,699 | 1/1979 | Collins et al. | 428/355 BL |
| 4,394,915 | 7/1983 | Nelson | 215/12.2 |
| 4,699,938 | 10/1987 | Minamizaki et al. | 524/271 |
| 5,037,411 | 8/1991 | Malcolm et al. | 604/358 |
| 5,523,343 | 6/1996 | Giordano et al. | 524/505 |
| 5,627,234 | 5/1997 | Giordano et al. | 525/89 |

FOREIGN PATENT DOCUMENTS

| | | | |
|---|---|---|---|
| 0358900 A1 | 7/1989 | European Pat. Off. | B32B 27/08 |
| 0368102 A2 | 10/1989 | European Pat. Off. | A61L 15/16 |
| 0656410 A1 | 11/1994 | European Pat. Off. | C09J 153/02 |
| 0669350 A1 | 2/1995 | European Pat. Off. | C08F 297/04 |
| 93/10734 | 9/1992 | WIPO | A61F 13/58 |

*Primary Examiner*—Peter A. Szekely
*Attorney, Agent, or Firm*—Donald F. Haas

[57] ABSTRACT

Hot melt adhesive compositions, comprising
(a) a radial multiarmed block copolymer $(AB)_nX$, wherein A is a block predominantly derived from a monovinylaromatic compound, B is a block predominantly derived from butadiene and which optionally has been partially or completely hydrogenated,
X is the residue of a multifunctional coupling agent,
n is in the range of from 3 to 6,
(b) a linear block copolymer AB, the components (a)+(b) being present in an amount of 100 parts by weight,
(c) a tackifying resin, which is compatible with the blocks B, in an amount of from 100 to 500 parts by weight,
(d) a plasticizer in an amount of from 100 to 300 parts by weight,
(e) an antioxidant-UV stabiliser in an amount from 0.1 to 5 parts by weight,
characterised in that the content of bound monovinylaromatic monomer in the block copolymers is at least 20%,
the vinyl content in the polymerised butadiene is at least 25%,
the diblock content, relative to the weight of components (a) and (b) is in the range of from 6 to 25%,
the diblock has an apparent molecular weight in the range of from 70,000 to 100,000 and the radial multiarmed block copolymer has an apparent molecular weight in the range of from 200,000 to 500,000, and disposable articles and pressure sensitive labels derived from them.

4 Claims, No Drawings

ADHESIVE COMPOSITIONS COMPRISING BLOCK COPOLYMERS OF A MONOVINYLAROMATIC COMPOUND AND BUTADIENE

This is a division of Application Ser. No. 08/812,226 filed Mar. 6, 1997, now U.S. Pat. No. 5,750, 607, the entire disclosure of which is hereby incorporated by reference.

FIELD OF THE INVENTION

The invention relates to adhesive compositions comprising block copolymers of a monovinyl aromatic compound, preferably styrene, and 1,3-butadiene. More in particular, the invention relates to adhesive compositions comprising a radial multiarmed block copolymer, wherein the arms contain at least one block derived from a monovinylaromatic monomer and at least one block derived from 1,3-butadiene monomer, obtained by coupling initially prepared livin arms by means of a multifunctional coupling agent. The invention relates to hot melt adhesive compositions.

BACKGROUND OF THE INVENTION

U.S. Pat. No. 5,037,411 disclosed the use of a hot melt adhesive composition for the multiline construction of disposable laminates, such as disposable diapers and feminine pads, said adhesive composition comprising:

(a) 5 to 15% by weight of a radial copolymer having three or four (AB) arms, wherein polymer blocks A are poly(styrene) blocks and polymer blocks B are poly (butadiene) or hydrogenated poly(butadiene) blocks having a molecular weight greater than 140,000 and containing at least 15 parts styrene per 100 parts of block copolymer, (b) 40 to 80% by weight of a compatible tackifying resin, (c) 5 to 30% by weight of a plasticizing oil, (d) 0 to 5% by weight of petroleum derived wax, and (e) 0.1 to 2% by weight of a stabiliser.

A preferred block copolymer to be used as component (a) was mentioned to be KRATON 1184, having a styrene content of 30%, but having a low vinyl content (<5%).

European patent application No. 0358900 teaches hot melt adhesive compositions suitable for disposable constructions, comprising:

(a) 10 to 40% by weight of a substantially radial styrene-butadiene block copolymer having a styrene content greater than 35% by weight, such as KRATON DX-1122, SOL-T162 LW/1 and SOL-T162 LW/2, (b) 20 to 65% by weight of at least one compatible tackifying resin, (c) 0.1 to 4% by weight of stabiliser, and (d) the remainder up to about 60% by weight, comprising at least one oil diluent.

"New Modified TPE Polymers" by D. J. Dougherty, Firestone Synthetic Rubber and Latex Company, Akron, USA (TAPPI Proceedings 1994 Hot Melt Symposium, 115–123, described the effect of vinyl modification in the range of from 30 to 50% on the relevant adhesive compositions containing styrene-butadiene block copolymers as compared to the properties of adhesive compositions containing the commercial block copolymer grade STEREON 840A, a linear multiblock copolymer. The Quick Stick property was found to be relatively unaffected by vinyl content up to 49%. 180° polyethylene peel was relatively constant up to 39% vinyl and then underwent a deterioration. 180° peel from stainless steel was fairly erratic, but generally increased with vinyl content. Polyken Tack was basically unaffected by vinyl content up to 49%, but was poor at 58% vinyl. The low adhesive viscosity was significantly improved by an increased in vinyl level. The adhesive tensile strength increased as the vinyl content was increased. However, no teaching at all was provided as to the interrelation of the adhesive properties and additional block copolymer manufacturing parameters such as styrene content, coupling agent, coupling efficiency, and molecular weights of the respective block constituents.

It will be appreciated that from an economical viewpoint there is still a need for further improvement of hot melt adhesive compositions to be used for disposable articles which composed of polymer film layers which are as thin as possible. Such hot melt adhesive compositions must, on the one hand, show a melt viscosity which is low enough for an efficient application on the substrate layers at the maximum processing temperature, governed by the thinner gauge polymer substrates, such as poly(ethylene) or poly (propylene), and, on the other hand, exhibit sufficiently high standard adhesive properties as prescribed by the consumer requirements and/or processing requirements.

An object of the present invention is therefore to provide such improved hot melt adhesive compositions for multiline construction or multidot construction of disposables by selection of block copolymers and tackifying resins and plasticizers as main ingredients for said adhesive compositions. As a result of extensive research and experimentation, said hot melt adhesive compositions surprisingly have been found.

SUMMARY OF THE INVENTION

Accordingly, the invention relates to hot melt adhesive compositions, comprising:

(a) a radial multiarmed block copolymer $(AB)_nX$, wherein A is a block predominantly derived from a monovinylaromatic compound, B is a block predominantly derived from butadiene and which optionally has been partially or completely hydrogenated, X is the residue of a multifunctional coupling agent, and n is in the range of from 3 to 6;

(b) a linear block copolymer AB, the components (a)+(b) being present in an amount of 100 parts by weight;

(c) a tackifying resin which is compatible with the blocks B in an amount of from 100 to 500 parts by weight;

(d) a plasticizer in an amount of from 100 to 300 parts by weight; and (e) an antioxidant -UV stabiliser in an amount from 0.1 to 5 parts by weight.

In these compositions the block copolymers are characterised by a content of bound monovinylaromatic monomer in the block copolymers of at least 20% by weight (wt %), a vinyl content in the polymerised butadiene of at least 25 wt %, a diblock content, relative to the weight of components (a) and (b), in the range of from 6 to 25 wt %, the diblock having an apparent molecular weight in the range of from 70,000 to 100,000. preferably from 70,000 to 90,000, and the radial multiarmed block copolymer having an overall apparent molecular weight in the range of from 200,000 to 500,000.

According to a preferred embodiment of the adhesive compositions of the present invention, multiarmed radial block copolymers having a monovinylaromatic monomer content of from 25 to 45 wt % are applied. According to another preferred embodiment of the adhesive compositions of the present invention, multiarmed radial block copolymers having a vinyl content in the polymerised butadiene in the range of from 40 to 60 wt % are applied. Another preferred embodiment of the present invention relates to the use of a diblock copolymer component (b) in an amount in the range of from 7 to 10 wt % relative to the weight of components (a) and (b).

DETAILED DESCRIPTION OF THE INVENTION

The molecular weights of linear polymers or unassembled linear segments of polymers such as mono-, di-, triblock, etc., arms of star polymers before coupling are conveniently measured by Gel Permeation Chromatography (GPC), where the GPC system has been appropriately calibrated. For anionically polymerized linear polymers, the polymer is essentially monodisperse (weight average molecular weight/number average molecular weight ratio approaches unity), and it is both convenient and adequately descriptive to report the "peak" (sometimes referred to as "apparent") molecular weight of the narrow molecular weight distribution observed. Usually, the peak (or apparent) value is between the number and the weight average. The peak (or apparent) molecular weight is the molecular weight of the main species shown on the chromatograph. For polydisperse polymers the weight average molecular weight should be calculated from the chromatograph and used. For materials to be used in the columns of the GPC, styrene-divinyl benzene gels or silica gels are commonly used and are excellent materials. Tetrahydrofuran is an excellent solvent for polymers of the type described herein. A refractive index detector may be used.

Measurement of the true molecular weight of the final coupled radial or star polymer is not as straightforward or as easy to make using GPC. This is because the radial or star shaped molecules do not separate and elute through the packed GPC columns in the same manner as do the linear polymers used for the calibration, and, hence, the time of arrival at a UV or refractive index detector is not a good indicator of the molecular weight. A good method to use for a radial or star polymer is to measure the weight average molecular weight by light scattering techniques. The sample is dissolved in a suitable solvent at a concentration less than 1.0 gram of sample per 100 milliliters of solvent and filtered using a syringe and porous membrane filters of less than 0.5 microns pore size directly into the light scattering cell. The light scattering measurements are performed as a function of scattering angle and of polymer concentration using standard procedures. The differential refractive index (DRI) of the sample is measured at the same wavelength and in the same solvent used for the light scattering. The following references are herein incorporated by reference:

1. *Modern Size-Exclusion Liquid Chromatography*, W. W. Yau, J. J. Kirkland, D. D. Bly, John Wiley & Sons, New York, N.Y., 1979.
2. *Light Scattering from Polymer Solution*, M. B. Huglin, ed., Academic Press, New York, N.Y., 1972.
3. W. Kaye and A. J. Havlik, *Applied Optics*, 12, 541 (1973).
4. M. L. McConnell, *American Laboratory*, 63, May, 1978.

The term "predominantly derived from monovinylaromatic compound" and "predominantly derived from butadiene" means that these major monomers can be mixed with minor amounts (<30 wt % and preferably <10%) of structurally similar or dissimilar comonomers. For example the monovinylaromatic monomer may consist of styrene, optionally mixed with minor amounts of comonomers selected from α-methystyrene, vinyltoluene, vinyl, xylene, ethyl vinylbenzene, as well as dicyclic monovinyl compounds, such as vinyl naphthalene and the like or combinations thereof or α-methylstyrene mixed with minor amounts of styrene or other before mentioned comonomers.

On the other hand, the styrene main monomer may be mixed with minor amounts of butadiene providing a random or tapered copolymer block. In an alternative way, the butadiene major monomer may be mixed with small amounts of isoprene or styrene, α-methylstyrene vinyltoluene, and the like.

Of the monomers to be used for the starting block copolymer components (a) and (b), it is preferred that substantially pure styrene and substantially pure butadiene are used for preparation of the blocks A and B, respectively. More preferably, the initially prepared living block copolymers $(AB)(^-)Li^+$ are coupled by means of a coupling agent selected from dimethyl adipate, diethyladipate, gamma-glycidoxy propyl trimethoxysilane, and tri-nonyl-phenyl phosphite, providing coupled block copolymers of an apparent molecular weight in the range of from 350,000 to 450,000. The use of gamma-glycidoxy propyl trimethoxysilane as coupling agent is preferred.

The coupling process is usually not 100 per cent effective. AB diblocks as described above are coupled (reacted) with the coupling agent. If less than all of the AB diblocks react, they will be left over in the reaction mixture. The overall success of this process is described as the "coupling efficiency" as is well known in the art. It is for this reason that the present invention describes the polymers used herein in terms of the coupled triblock and the left over uncoupled diblock. Thus, the total polymer in the adhesive composition is described as the amount of (a) plus (b) above.

It will be appreciated that the predominantly poly (butadiene) block in the complete coupled block copolymer and in the remaining non coupled diblock copolymer optionally may be selectively hydrogenated, i.e. without any substantial hydrogenation of the aromatic unsaturation in the blocks A, to a certain degree of the original ethylenic unsaturation by methods known per se, such as disclosed in e.g. European Patent Application Nos. 0544304A, 0545844A, 0601953A, British Patent Application No. 2,159.819A, European Patent Application No. 0434469A, which are herein incorporated by reference.

It is necessary to add an adhesion promoting or tackifying resin that is compatible with the elastomeric poly(butadiene) blocks B in the block copolymer ingredients. Tackifying resins useful in the adhesives of the invention comprise rosin derivatives including wood rosin, tall oil, tall oil derivatives, rosin ester resins, natural and synthetic terpenes, and aliphatic or mixed aliphatic-aromatic tackifying resins.

Aliphatic monomers useful in forming tackifying resins are typical natural and synthetic terpenes which contains $C_5$ and $C_6$ cyclohexyl or cyclopentyl saturated groups that can additionally contain a variety of substantial aromatic ring substituents. Aliphatic tackifying resins can be made by polymerising a feed stream containing sufficient aliphatic monomers such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-1,3-butadiene, 2-methyl-2-butene, cyclopentadiene, dicyclopentadiene, terpene monomers, and others.

The adhesive compositions of the invention can contain rosin and rosin derivatives as a tackifying agent. Rosin is a solid material that occurs naturally in the oleo rosin of pine trees and typically is derived from the oleo resinous exudate of the living tree, from aged stomps and from tall oil produced as a by-product of kraft paper manufacture. After it is obtained rosin can be treated by hydrogenation, dehydrogenation, polymerisation, esterification, and other post treatment processes. Rosin is typically classed as a gum rosin, a wood rosin, or as a tall oil rosin which indicate its source. The material can be used unmodified, in the form of esters of polyhydric alcohols, and can be polymerised through the inherent unsaturation of the molecules. Materials are commercially available and can be blended into the adhesive compositions using standard blending techniques. Representative examples of such rosin derivatives include pentaerythritol esters of tall oil, gum rosin, wood rosin, or mixtures thereof.

Representative examples of such aliphatic resins include hydrogenated synthetic $C_9$ resins, synthetic branched and unbranched $C_5$ resins and mixtures thereof. Representative examples of such aromatic tackifying resins include styrenated terpene resins, styrenated $C_5$ resins or mixtures thereof. The selection of tackifying resins is often based on the nature of the B or midblock radial block copolymer. Rosin derivatives can be used with S-B-S blends. For S-B-S copolymers, styrenated terpenes or rosin esters are preferred. Preferred component (c) tackifying resins are selected from $C_5$ resin, a styrenated terpene resin, a hydrogenated $C_9$ resin a natural rosin, a rosin derivative or mixtures thereof. More preferably the resin component (c) is selected from Aromatic monomers useful in forming mixed aliphatic-aromatic tackifying resins useful in this invention can be prepared from any monomer containing substantial aromatic qualities and a polymerizable unsaturated group. Typical examples of such aromatic monomers include the styrenic monomers, styrene, alphamethylstyrene, vinyl toluene, methoxystyrene, tertiary butyl styrene, chlorostyrene, etc., indene monomers, including indene, methyl indene, and others. Mixed aliphatic-aromatic resins contain sufficient aromatic monomers and sufficient aliphatic monomers and optionally other $C_3$–$C_8$ unsaturated monomers to produce a resin having both aliphatic and aromatic character.

Plasticizing oils are used in the adhesives of the invention. Such oils are primarily hydrocarbon oils low in aromatic content. Preferably the oils are paraffinic or naphthenic in character. The oils are preferably low in volatility, are clear and have a little colour and odour as possible. The use of a plasticizing oil of this invention also contemplates the use of olefin oligomers, low molecular weight polymers, vegetable oils and their derivatives and similar plasticizing liquids. The use of olefin oligomers such as HYVIS (trademark) or NAPVIS (trademark) polymers, or paraffinic oils is preferred.

Plasticizing oils used in adhesive compositions can be prevented from migration by the use of gelling or complexing agents which end to restrain the migration of oil through formations of gels or complexes. The oil can be restrained by a variety of gelling agents including waxes, polyethylene waxes, oxidised waxes, oxidised polyethylene waxes, polyvalent metal soaps, etc.

It has been found, that effective commercial manufacture of the hot melt adhesives of this invention using high molecular weight radial block copolymers involves a two-step manufacturing procedure. In the first step the radial block copolymer is mixed at elevated temperature with at least one additional adhesive component such as a tackifier, plasticizers, or mixtures thereof to form a preblend or a premix wherein the block copolymer is intimately mixed with the other adhesive ingredient. The preblend is then blended with the remaining adhesive components at elevated temperature in standard commercial blending equipment.

In somewhat greater detail, from about 0.5 parts by weight of resin to about 2.5 parts by weight of resin can be blended per part by weight of radial block copolymer in order to form the preblend of the invention. The preblends can be prepared in conventional thermoplastic polymer processing equipment capable of providing sufficiently high shear to intimately blend the high molecular weight polymers and the low molecular weight adhesive components such as tackifying resins, oils or other low molecular weight polymeric materials or blends thereof. Examples of such equipment are single or twin screw extruders, intensive internal mixers, Mixtruders, Sigma Blade mixers, and the like, which may be heated to a sufficient processing temperature, typically between 121°–177° C. If a batch mixer is used, the polymer is blended with the adhesive component such as resin, oil or component blends thereof, typically at an amount less than or equal to the polymer to provide a homogeneous preblend. Thereafter the remaining ingredients can be added and mixed until homogeneous. The equipment and processes useful in the manufacture of the preblend materials of the invention are generally known in the art.

According to a preferred embodiment of the compositions of the present invention the radial multiarmed block copolymer, component (a) has an apparent molecular weight in the range of from 350,000 to 500,000. Also preferably, the blocks A and B are derived from substantially pure styrene monomer and of substantially pure 1,3 butadiene or isoprene monomer respectively. According to another preferred embodiment of the present hot melt adhesive compositions block copolymer, component (a) is obtained by coupling of living AB block copolymers with dimethyl adipate, diethyl adipate, gamma-glycidoxy-propyl-trimethoxysilane or trinonyl-phenyl phosphite.

According to another preferred embodiment of the present hot melt adhesive compositions, the block copolymer components (a) and (b) comprise hydrogenated B blocks, whereas the aromatic unsaturation in the A blocks have not been hydrogenated in significant degree. More preferably, the blocks B have been hydrogenated up to a degree of 5% or less of the original residual ethylenic unsaturation whereas the aromatic unsaturation in the A blocks is maintained on 95% of the original residual aromatic unsaturation or more.

It will be appreciated that another aspect of the present invention is formed by disposable articles of multiline or multidot construction, obtainable by using the hot melt adhesive compositions as specified hereinbefore. More in particular, this aspect of the present invention relates to disposable articles comprising at least one polyethylene or polypropylene substrate bound to at least one tissue, nonwoven polyethylene or polypropylene substrate. Another aspect of the present invention is formed by pressure sensitive adhesive labels obtainable by coating a substrate layer on at least one side with a hereinbefore specified hot melt adhesive composition.

The invention is further illustrated by the following examples and comparative examples, however without restricting its scope to these embodiments.

EXAMPLES

Adhesive formulations were prepared from the ingredients as listed below:

A

A1—100 parts by weight of a commercially available triblock copolymer comprising arms consisting of poly(styrene) blocks and poly(butadiene) blocks, having a poly(styrene) content of 37 wt %, a coupling efficiency of 90 wt %, and a total apparent molecular weight of 138,000.

A2—255 parts by weight of a poly(butadiene) block modifying resin REGALREZ R91.
A3—45 parts by weight of plasticizing oil (ONDINA 68).
A4—1 part by weight of antioxidant (IRGANOX)

B
B1—100 parts by weight of a triblock copolymer suitable for the present invention comprising arms containing poly(styrene) blocks and poly(butadiene) blocks, having a vinyl content of 49%, coupled by means of gamma glycidoxy-propyl-trimethoxysilane, and having a coupling efficiency of 92% and a polystyrene content of 30%, and component B2, B3 and B4, being the same as the components A2, A3, A4.

C
C1—100 parts by weight of the triblock copolymer as specified under B1.
C2—176 parts by weight of the poly(butadiene) block modifying resin (REGALREZ R91).
C3—48 parts by weight of the plasticizing oil (ONDINA 68).
C4—1 part by weight of antioxidant (IRGANOX 1010)

The following properties were measured before and after aging of the composition samples.

|  |  | no aging | | | 1 week aging | | | 2 weeks aging | | |
|---|---|---|---|---|---|---|---|---|---|---|
| Comp. |  | A | B | C | A | B | C | A | B | C |
| Tg | °C. | −10 | 0 | −10 | id | id | id | id | id | id |
| LT | N/mm$^2$ | 0 | 6a | 19 | 0 | 1$^a$ | 10 | 0 | 1$^a$ | 10 |
| PA | N/mm$^2$ | 0 | 32$^b$ | 21 | 0 | 22$^b$ | 18 | 0 | 21$^b$ | 15 |
| HP 2 kg | hrs | 0 | >100 | 40 | 0 | 70 | 12 | 0 | 55 | 7 |
| HP 95° C. | hrs | 0 | 16 | 50 | 0 | 8 | 55 | 0 | 14 | 64 |
| SAFT | °C. | 0 | 119 | 130 | 0 | 122 | 130 | 0 | 122 | 63 | a: zippery tack
b: cohesion failure

We claim:

1. A disposable article of multiline or multidot construction obtainable by application of a hot melt adhesive comprising:
   (a) a radial multiarmed block copolymer (AB)$_n$X, wherein A is a block predominantly derived from a monovinylaromatic compound, B is a block predominantly derived from butadiene, wherein X is the residue of a multifunctional coupling agent and n is in the range of from 3 to 6,
   (b) a linear block copolymer AB, wherein the components (a)+(b) are present in an amount of 100 parts by weight,
   (c) a tackifying resin, which is compatible with the blocks B, in an amount of from 100 to 500 parts by weight,
   (d) a plasticizer in an amount of from 100 to 300 parts by weight,
   (e) an antioxidant-UV stabiliser in an amount from 0.1 to 5 parts by weight,
   characterised in that the content of bound monovinylaromatic monomer in the block copolymers is at least 20 wt %,
   the vinyl content in the polymerised butadiene is at least 25 wt %,
   the diblock content, relative to the weight of components (a) and (b), is in the range of from 6 to 25 wt %, the diblock has an apparent molecular weight in the range of from 70,000 to 100,000, and the radial multiarmed block copolymer has an overall apparent molecular weight in the range of from 200,000 to 500,000.

2. The disposable article of claim 1 comprising at least one polyethylene or polypropylene substrate bound to at least one tissue non-woven, polyethylene, or polypropylene substrate.

3. The disposable article of claim 2 rselected from the group consisting of sanitary napkins and bed pads.

4. Pressure sensitive adhesive labels characterized in that they are obtainable by coating a substrate layer on at least one side with an adhesive compositions comprising:
   (a) a radial multiarmed block copolymer (AB)$_n$X, wherein A is a block predominantly derived from a monovinylaromatic compound, B is a block predominantly derived from butadiene, wherein X is the residue of a multifunctional coupling agent and n is in the range of from 3to 6,
   (b) a linear block copolymer AB, wherein the components (a)+(b) are present in an amount of 100 parts by weight,
   (c) a tackifying resin, which is compatible with the blocks B, in an amount of from 100 to 500 parts by weight,
   (d) a plasticizer in an amount of from 100 to 300 parts by weight,
   (e) an antioxidant-UV stabiliser in an amount from 0.1 to 5 parts by weight,
   characterised in that the content of bound monovinylaromatic monomer in the block copolymers is at least 20 wt %,
   the vinyl content in the polymerised butadiene is at least 25 wt %,
   the diblock content, relative to the weight of components (a) and (b), is in the range of from 6 to 25 wt %, the diblock has an apparent molecular weight in the range of from 70,000 to 100,000, and the radial multiarmed block copolymer has an overall apparent molecular weight in the range of from 200,000 to 500,000.

* * * * *